(12) United States Patent
Sprenger et al.

(10) Patent No.: US 8,447,013 B2
(45) Date of Patent: May 21, 2013

(54) MULTIBEAM X-RAY SOURCE WITH INTELLIGENT ELECTRONIC CONTROL SYSTEMS AND RELATED METHODS

(75) Inventors: Frank Sprenger, Cary, NC (US); Moritz Beckmann, Cary, NC (US); Yuan Cheng, Cary, NC (US); Houman Jafari, Cary, NC (US)

(73) Assignee: XinRay Systems Inc, Research Triangle Park, NC (US)

( * ) Notice: Subject to any disclaimer, the term of this patent is extended or adjusted under 35 U.S.C. 154(b) by 215 days.

(21) Appl. No.: 13/069,286

(22) Filed: Mar. 22, 2011

(65) Prior Publication Data

US 2011/0286581 A1   Nov. 24, 2011

Related U.S. Application Data

(60) Provisional application No. 61/340,798, filed on Mar. 22, 2010.

(51) Int. Cl.
*H01J 35/00* (2006.01)
(52) U.S. Cl.
USPC ............................ 378/122; 378/134; 378/136
(58) Field of Classification Search
USPC .................................. 378/122, 134, 136, 119
See application file for complete search history.

(56) References Cited

U.S. PATENT DOCUMENTS

| 6,456,691 B2 * | 9/2002 | Takahashi et al. ............ 378/122 |
| 7,826,595 B2 * | 11/2010 | Liu et al. ....................... 378/122 |
| 2010/0290593 A1 * | 11/2010 | Legagneux et al. ........... 378/122 |

OTHER PUBLICATIONS

Written Opinion of the International Preliminary Examining Authority for Application Serial No. PCT/US2011/029460 dated Feb. 16, 2012.
International Preliminary Report on Patentability Dated May 2, 2012 for Application Serial No. PCT/US2011/029460.

* cited by examiner

*Primary Examiner* — Hoon Song
(74) *Attorney, Agent, or Firm* — Jenkins, Wilson, Taylor & Hunt, P.A.

(57) ABSTRACT

Multibeam field emission x-ray systems and related methods can include cathode elements, an anode assembly spaced from the plurality of cathode elements, and an extraction gate positioned between the plurality of cathode elements and the anode assembly. A potential difference can be applied between the extraction gate and at least one of the cathode elements to cause an emission of electrons from the respective cathode elements. Emission characteristics of the cathode elements can be measured, and the potential difference between the extraction gate and at least one of the cathode elements can be adjusted based on the emission characteristics measured.

24 Claims, 10 Drawing Sheets

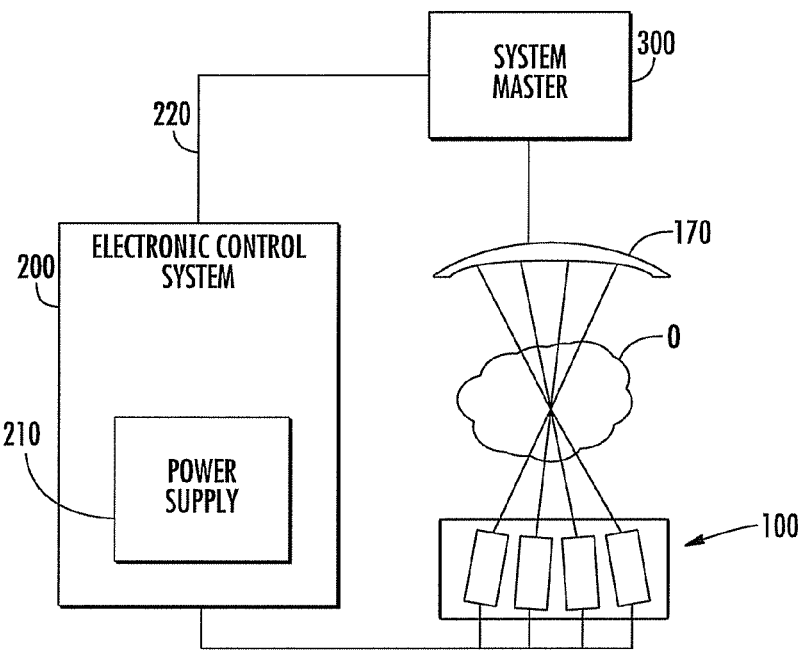
FIG. 5
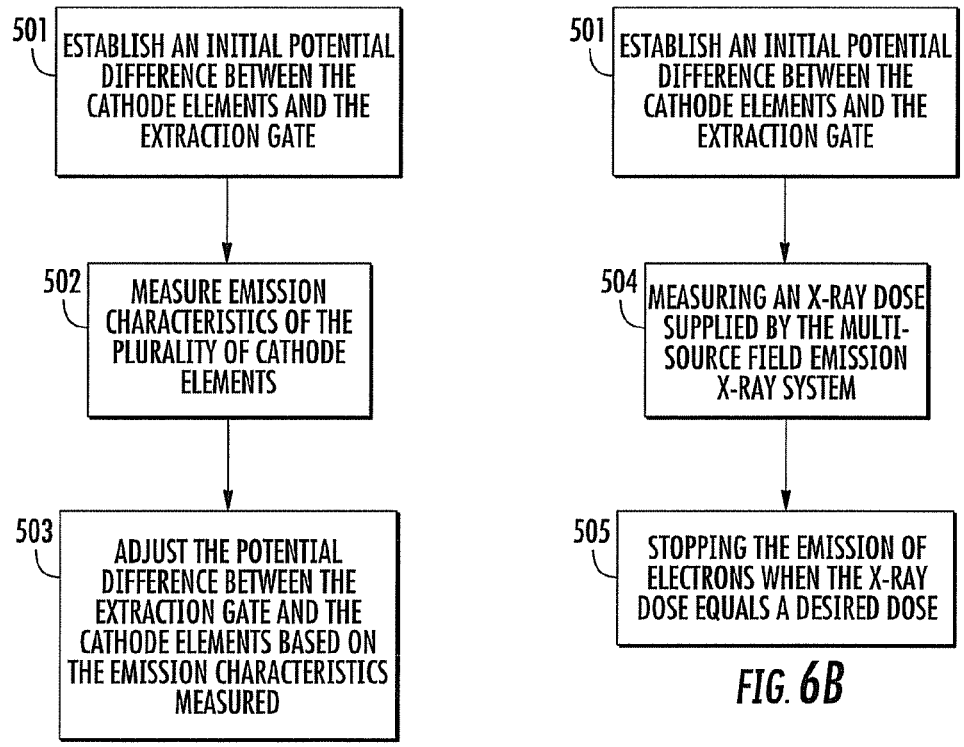
FIG. 6A
FIG. 6B

MULTIBEAM X-RAY SOURCE WITH INTELLIGENT ELECTRONIC CONTROL SYSTEMS AND RELATED METHODS

RELATED APPLICATION

The presently disclosed subject matter claims the benefit of U.S. patent application Ser. No. 61/340,798, filed Mar. 22, 2010, the disclosure of which is incorporated herein by reference in its entirety.

TECHNICAL FIELD

The subject matter disclosed herein relates generally to x-ray imaging. More particularly, the subject matter disclosed herein relates to multibeam field emission x-ray systems and related control systems and methods.

BACKGROUND

X-ray radiation is widely used to probe the internal structure of materials in applications such as medical diagnosis, security screening, and industrial inspection. X-rays can also be used for radiation treatment procedures (e.g. to destroy tumors or to sterilize packages). In simple imaging methods, x-ray photons are transmitted through an object. The transmitted x-ray photons collected by a recording device over a period of time form a static projection image with overlapping structural features. More advanced imaging methods, such as tomosynthesis or computed tomography (CT), use multiple projection images from different viewing angles for image reconstruction or multiple frame images for contrast enhancement purposes.

Typical CT scanners achieve multiple viewing angles by high-speed rotation of an x-ray tube around an object. This requires a large and complicated gantry, which limits current medical CT scanners to about three rotations per second. Due to the gantry rotation the source has to move on a circular trajectory. Moreover, the image acquisition is limited to a sequential recording of x-ray images.

A multibeam x-ray source can be used to obtain projection images of an object from different viewing angles without mechanical motion of the source and with the potential for faster image acquisition speed. Although a multibeam x-ray source can provide these advantages, however, a multibeam source alone does not address the potential problem that many independent source elements need to be controlled and potential electron generation element degradation resulting in changes in the output of the x-ray source, need to be monitored and if necessary corrected. Accordingly, it would be desirable for a multibeam x-ray source to provide more consistent and predictable x-ray output combined with good system integration and interfacing.

SUMMARY

In accordance with this disclosure, systems and methods for controlling a multibeam field emission x-ray system are provided. In one aspect, a method for performing an x-ray scan is provided. A multibeam field emission x-ray system can be provided, and the system can comprise a plurality of cathode elements, an anode assembly spaced from the plurality of cathode elements, and an extraction gate positioned between the plurality of cathode elements and the anode assembly. Using this system, a potential difference can be applied between the extraction gate and at least one of the plurality of cathode elements to cause an emission of electrons from the respective cathode elements. Emission characteristics of the plurality of cathode elements can be measured, and the potential difference between the extraction gate and at least one of the plurality of cathode elements can be adjusted based on the emission characteristics measured.

In another aspect, a multibeam field emission x-ray system can be provided. The system can comprise a plurality of cathode elements, an anode assembly spaced from the plurality of cathode elements, an extraction gate positioned between the plurality of cathode elements and the anode assembly, and an electronic control system. The electronic control system can be configured to control an application of a potential difference between the extraction gate and at least one of the plurality of cathode elements to cause an emission of electrons from the respective cathode elements, to measure emission characteristics of the plurality of cathode elements, and to adjust the potential difference between the extraction gate and at least one of the plurality of cathode elements based on the emission characteristics measured.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 5 is a schematic illustration of a multibeam field emission x-ray system according to an embodiment of the presently disclosed subject matter;

FIGS. 6A and 6B are flow charts illustrating steps in two methods of controlling a multibeam field emission x-ray system according to embodiments of the presently disclosed subject matter.

DETAILED DESCRIPTION

Figure 1:
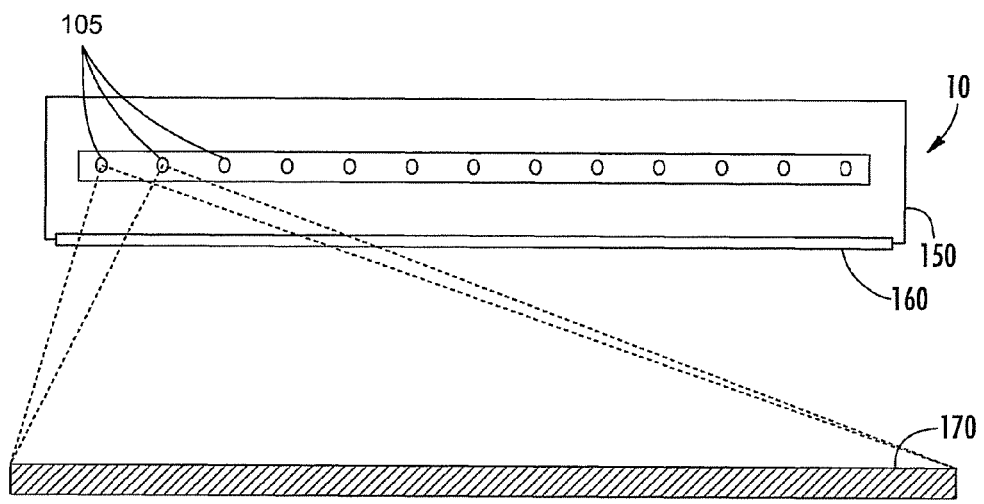
FIG. 1 is a cutaway view of a multibeam field emission x-ray system according to an embodiment of the presently disclosed subject matter.
Figure 2A:
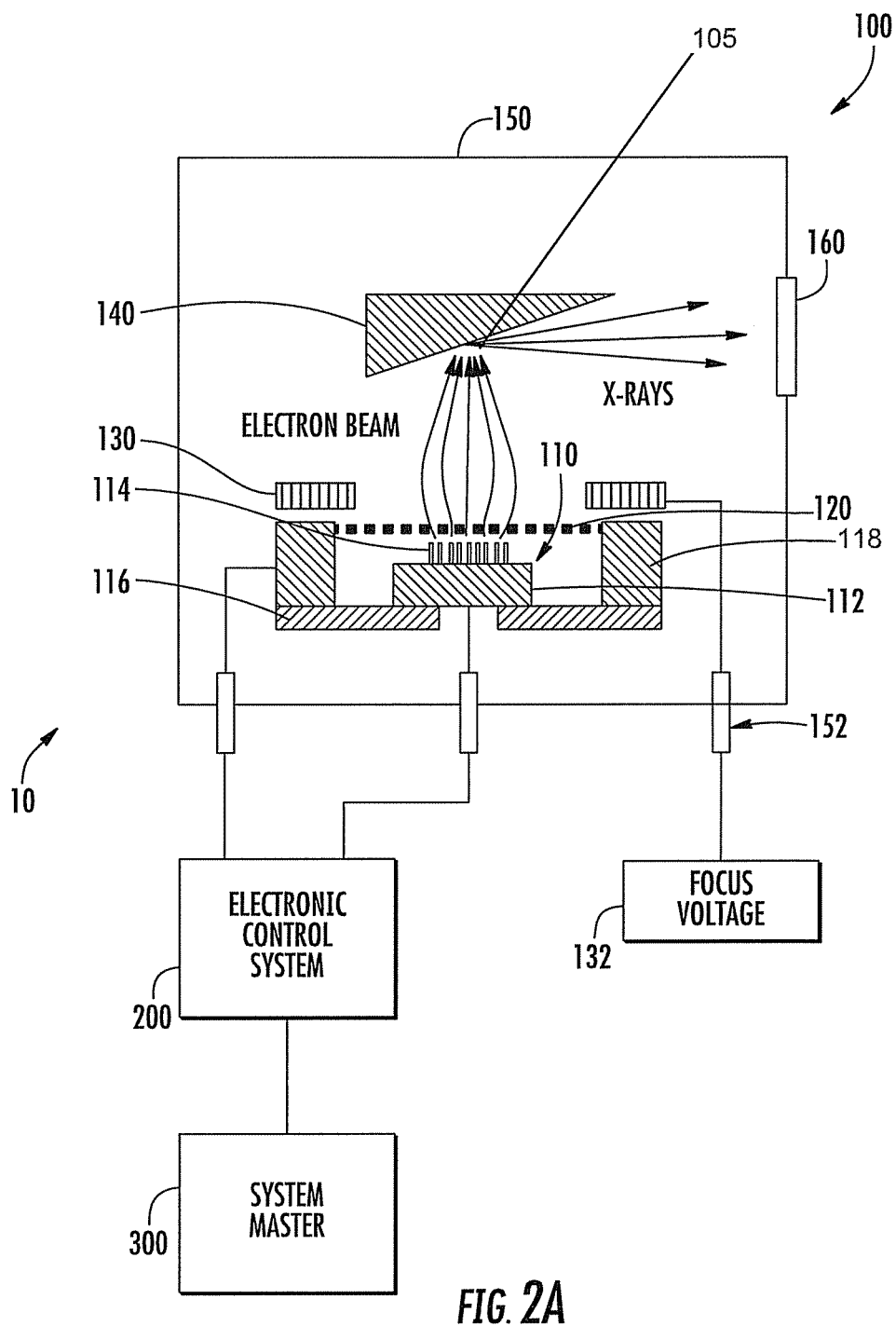
FIGS. 2A and 2B are cutaway views of a field emission x-ray source for use in a multibeam field emission x-ray system according to two embodiments of the presently disclosed subject matter.
Figure 2B:
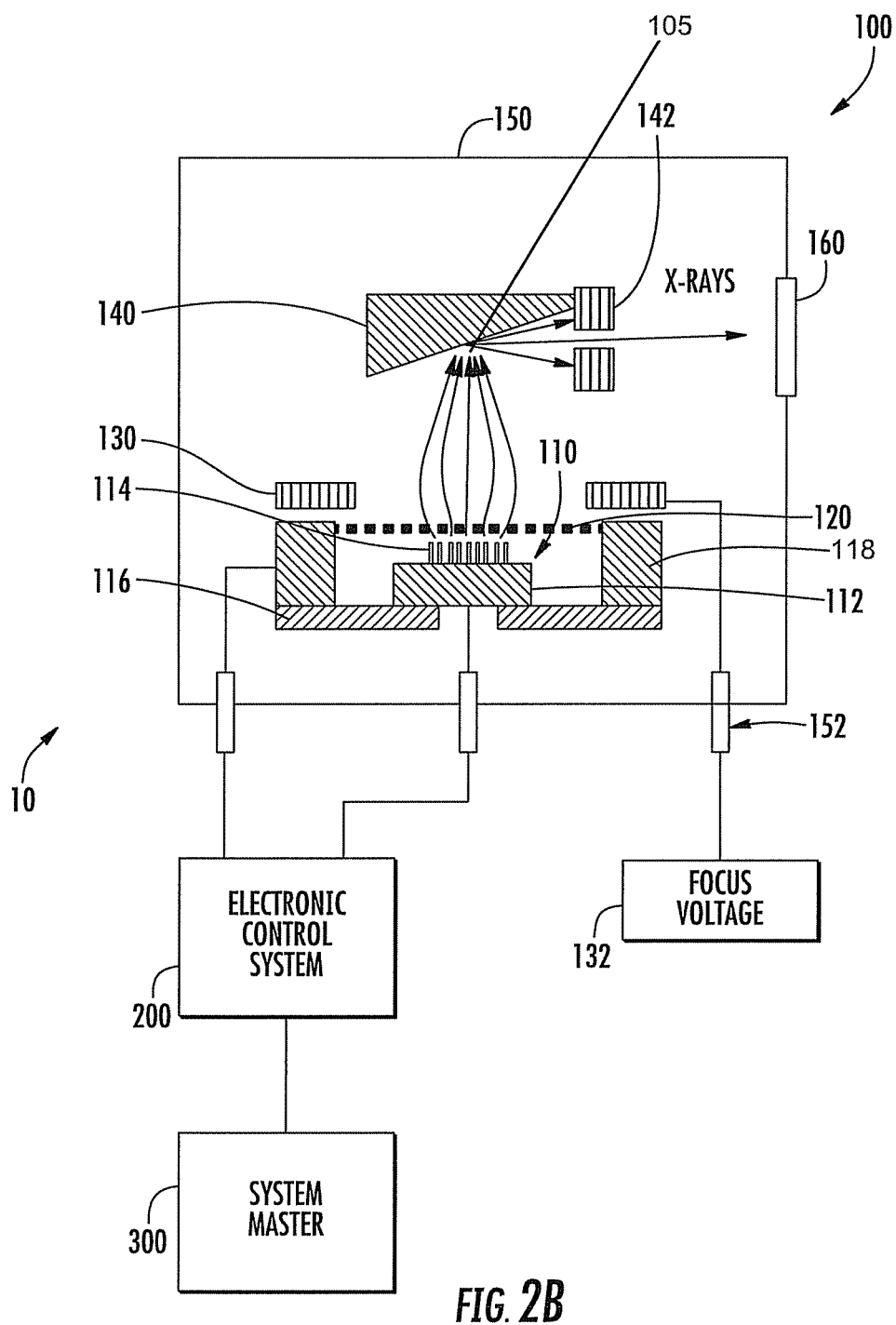

The present subject matter provides systems and methods for controlling a multibeam field emission x-ray system. In one aspect, the present subject matter provides a multibeam field emission x-ray system, generally designated 10. Referring to FIGS. 1, 2A and 2B, for example, multibeam field emission x-ray system 10 can comprise a plurality of x-ray beam focal spots 105, created from individual field emission x-ray sources 100. In the exemplary configuration shown in FIG. 2A, each x-ray source 100 can comprise a cathode element 110, each of which in turn comprising a substrate 112 with a carbon nanotube (CNT) field emission film 114 on an insulating material 116 (e.g. glass or ceramics). Examples of such a field emission cathode formed at least partially from a nanostructure-containing material can be found in U.S. Pat. No. 6,553,096, the disclosure of which is incorporated herein in its entirety.

Figure 3:
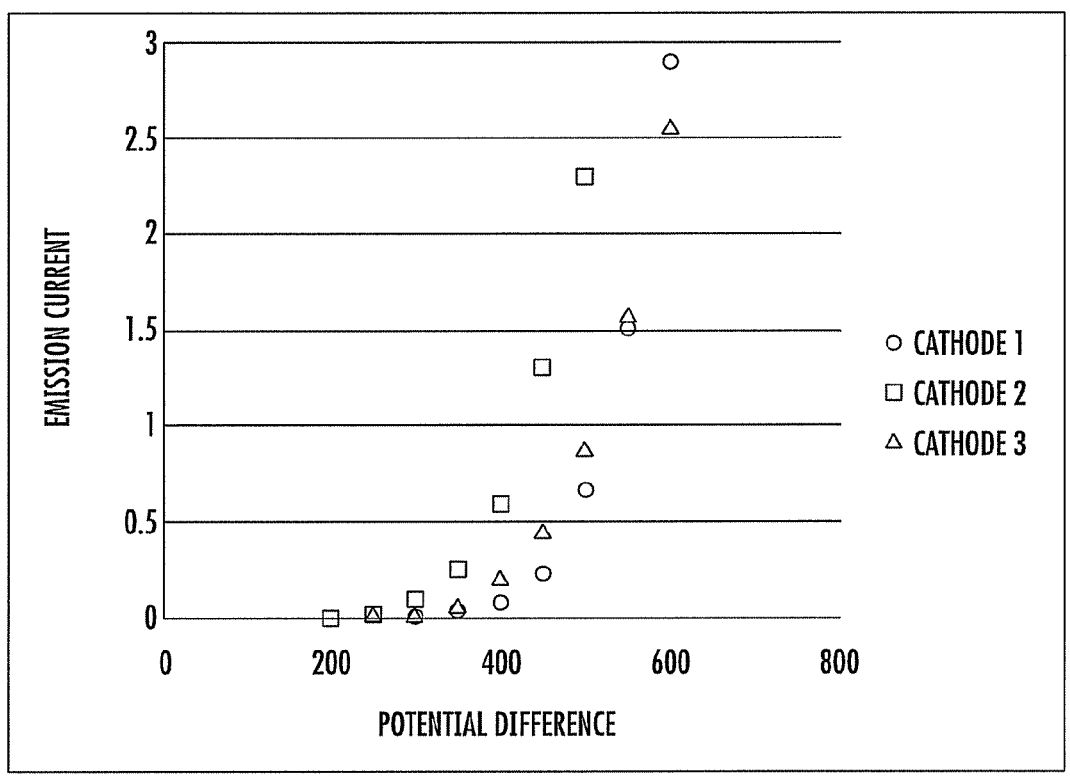
FIG. 3 is a graph showing emission behavior of a field emission cathode over a range of applied potential differences.

Spaced from the surface of cathode elements 110 by a spacing element 118, an electron extraction gate 120 can be positioned at a predetermined distance. For example, extraction gate 120 can be a metal mesh structure that can be positioned between about 50 to 500 µm from and parallel to cathode elements 110. Extraction gate 120 can be electrically insulated from cathode elements 110, in particular from substrate 112. A common extraction gate 120 can be shared for all of x-ray sources 100, or multiple individual extraction gates or a segmented gate can be used as discussed in further detail hereinbelow. By applying a potential difference between extraction gate 120 and cathode elements 110, electrons can be generated by field emission. Specifically, the emission of electrons can be controlled by regulating a potential difference between cathode elements 110 and extraction gate 120 to be at or above a certain emission threshold. If the potential difference is below this threshold, no significant emission takes place. As shown in FIG. 3, this emission behavior can be described approximately by the Fowler-Nordheim equation. In some approximations, the emitted electron current can be proportional to the exponential of the applied potential difference (i.e., I-V-dependence). Because of the exponential dependence, precise regulation of the applied potential can help to achieve the desired current or to maintain a constant electron emission current. Moreover, the I-V-dependence of individual emitters can vary from cathode to cathode.

In addition, referring again to FIG. 2A, a focusing structure 130 can be spaced from cathode elements 110 and extraction gate 120 for focusing the emitted electron beam onto an anode 140 (e.g., an anode comprising a tungsten target material). Anode 140 can be a reflection or transmission target. Focusing can be passive (i.e., focusing structure 130 supplied with same potential as extraction gate 120) or active (i.e., with one or more focus planes on different potentials) with a voltage supplied by a focusing voltage source 132. Focusing voltage source 132 can be independent from the power source that applies a potential difference between extraction gate 120 and cathode elements 110, or it can be connected to a common source. Anode 140 can be supplied with a positive potential relative to cathode elements 110 and can be positioned at a predetermined distance from cathode elements 110. For instance, the distance between cathode elements 110 and anode 140 can be selected to be large enough to provide desirable electrical insulation. By extracting electrons from cathode elements 110 and accelerating the electrons to anode 140, x-rays are produced. In addition, FIG. 2B illustrates another embodiment of x-ray system 10, in which an anode-side collimator 142 can be positioned between anode 140 and x-ray window 160, particularly in configurations in which an outside collimator is not feasible.

Figure 2C:
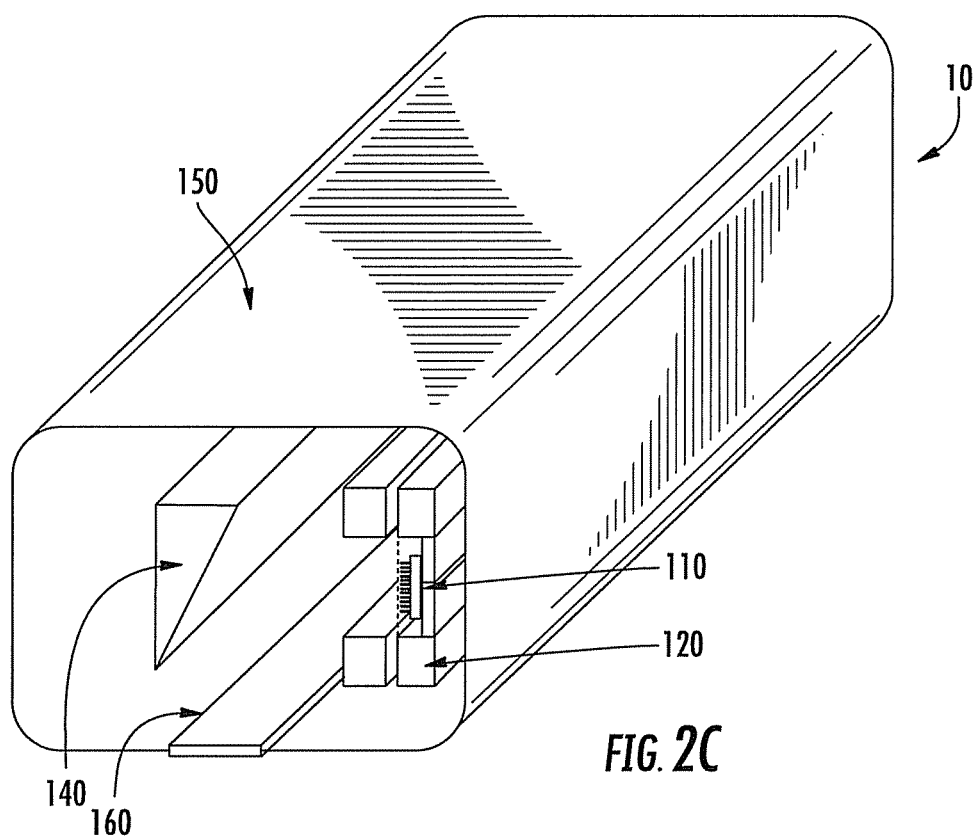
FIG. 2C is a cutaway perspective view of a multibeam field emission x-ray system according to one embodiment of the presently disclosed subject matter.

In either configuration, cathode elements 110, extraction gate 120, and anode 140 can be placed in a vacuum housing 150. As shown in FIG. 2C, vacuum housing 150 can be provided as an elongated, linear tube in which all of x-ray sources 100 can be housed. Referring again to FIGS. 2A and 2B, vacuum housing 150 can comprise electrical feedthroughs 152 that allow individual electrical connections to be made to the components contained therein. Specifically, an electronics control system 200 can be connected to one or more of cathode elements 110 or extraction gate 120. As discussed above, in order to extract electrons from an individual field emission source, electronic control system 200 can apply a potential difference between cathode elements 110 and extraction gate 120. For example, electronics control system 200 can be connected to both cathode elements 110 and extraction gate 120 for specifically applying a potential difference between the two components. Alternatively, extraction gate 120 can be connected to a ground, and electronic control system 200 can establish a negative potential on cathode elements 110.

For a large number of cathode elements, it is recognized that the electrical connections can get complicated because a large number of channels on electronic control system 200 and electrical feedthroughs 152 in vacuum housing 150 can be required. Specifically, for N cathode elements, a minimum of N+1 channels and connections would be required (e.g., one for each of cathode elements 110, and one for extraction gate 120, plus any additional feedthrough connections for focusing structure 130). Each of electrical feedthroughs 152 can be designed to insulate the voltage applied to extraction gate 120, which can be on the order of 1 to 3 kV.

Figure 4A:
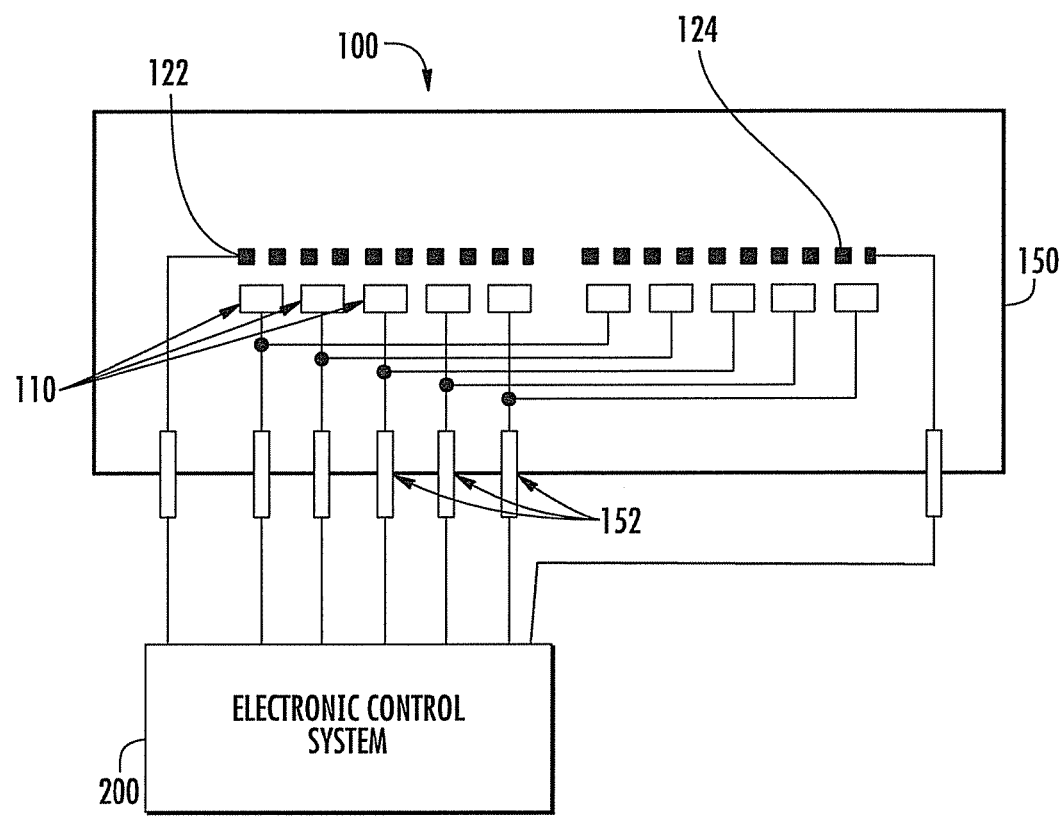
FIGS. 4A and 4B are schematic illustrations of a field emission x-ray source for use in a multibeam field emission x-ray system according to embodiments of the presently disclosed subject matter.

Accordingly, one way to reduce the number of electrical feedthroughs 152 used can involve extraction gate 120 being segmented into a plurality of gate segments. For example, as shown in FIG. 4A, rather than a single extraction gate 120 shared among all of x-ray sources 100, multibeam field emission x-ray system 10 can comprise a first gate segment 122 and a second gate segment 124, but further segments can also be provided where desired. Both of first gate segment 122 and second gate segment 124 can be connected to electronic control system 200, and the cathode feedthroughs can be shared because the extraction voltage is only applied to one of the two gate segments.

Figure 4B:
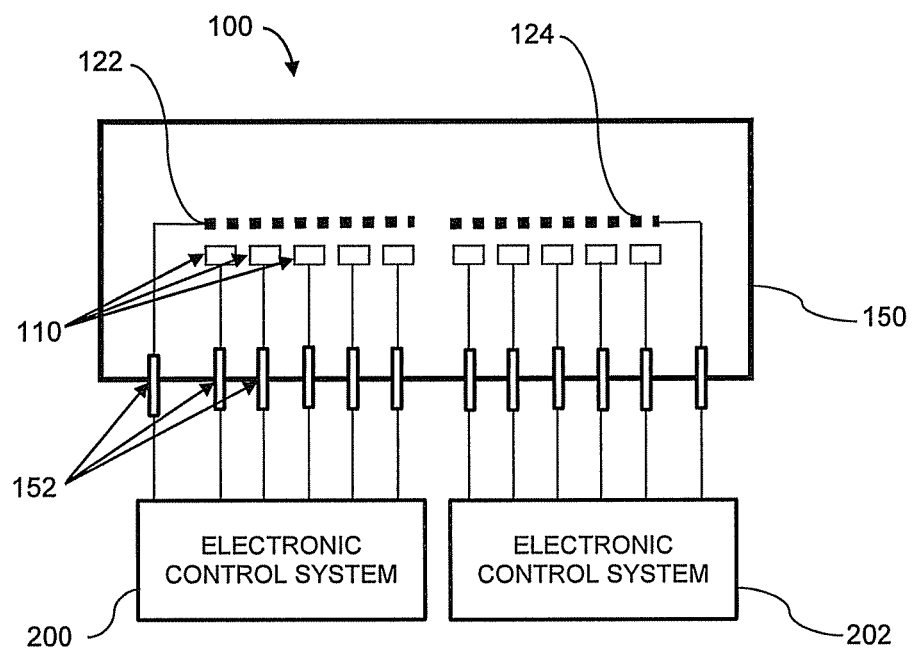

In another example, as shown in FIG. 4B, first gate segment 122 can be controlled by electronic control system 200 and second gate segment 124 can be controlled by a second electronic control system 202 that can be separate and independent from electronic control system 200 and can be identically or similarly structured and operable. This can be used to drive two or more cathodes simultaneously. Of course, it should be recognized that any of a variety of different control configurations can be used.

Regardless of the specific configuration, this segmenting of the extraction gate can allow grouping of the cathode connections and a reduction in the total number of required electrical connections required. For example, for a total number of N cathode elements 110 with S gate segments (e.g., first and second gate segments 122 and 124), only N/S+S connections are required. In addition, S cathode elements 110 can share a common electrical feedthrough 152. In this configuration, electronic control system 200 can comprise N/S channels for the substrate potential and S channels for the gate segments. Using combinations of gate channels and cathode channels, cathode elements 110 can still be individually addressed, but with fewer electrical feedthroughs 152.

In configurations where extraction gate 120 is grounded, it is noted that gate segmentation is not as easily achievable. Extraction gate 120 can be segmented and isolated from the vacuum housing 150, however, and only activated gate segments can be connected to ground by electronic control system 200. Inactive gate segments can be switched to a negative potential that is close to the potential applied to corresponding cathode elements 110. Regardless of the specific configuration, it can be advantageous that all connections have a large cross section with a low resistance.

For an imaging application, one or more of x-ray sources 100 can be turned on and off in any of a variety of prearranged sequences in order to acquire a series of x-ray images or signals related to the x-ray exposure. For example, electronic control system 200 can provide switching of x-ray sources 100 on and off for a certain time, either individually or in combination together. In one particular example, x-ray sources 100 can be switched in a pulsed operation mode, with pulse durations ranging from about 10 μs to several seconds or longer. In another particular example, electronic control system 200 can provide switching of all of x-ray sources 100 simultaneously.

Electronic control system 200 can further have a built in circuit that allows an accurate current control over the desired pulse length for each of x-ray sources 100. In addition, as shown in FIG. 5, electronic control system 200 can control the output of a power supply 210 connected to one or more of cathode elements 110, extraction gate 120, or anode 140. For example, in one configuration, extraction gate 120 can be connected to power supply 210, and electronic control system 200 can control power supply 210 to apply a static voltage to extraction gate 120. Alternatively, in another exemplary configuration, extraction gate 120 can be connected to a ground potential, and electronic control system 200 can control power supply 210 to apply a negative potential to cathode elements 110. As noted above, power supply 210 can be independent from focusing voltage source 132 discussed above, or they can be integrated together. Similarly, electronic control system 200 can be used to control focusing voltage source 132 in addition to power supply 210, or an independent control system can be used.

Electronic control system 200 can also be equipped with electrical interfaces 220 that can allow communication with an imaging or treatment device 170 positioned to receive and measure either or both of the x-rays transmitted through an object O or the backscattered photons from object O. For instance, such an electrical interface 220 can comprise real-time signals for synchronization of x-ray sources 100 with a system master 300 that controls imaging or treatment device 170. In one particular example, where imaging or treatment device 170 is an x-ray detector, the images acquired can be used individually, or they can be combined to reconstruct a 3D image of object O (i.e., tomography or tomosynthesis). Alternatively or in addition, electrical interfaces 220 can comprise a data channel for transferring information between electronics control system 200 and system master 300. This information can include scan parameters (e.g., pulse duration, duty cycle, current amplitude, or dose for each cathode channel), status, and/or error information.

With multibeam field emission x-ray system 100 having a configuration as described above, an x-ray scan can be performed by establishing an initial potential difference between one or more of cathode elements 110 and extraction gate 120 (see step 501 in FIGS. 6A and 6B), the initial potential difference being based on stored I-V-data for the desired output current, which can be set by system master 300 prior to each scan. From this initial state, any of a variety of operational modes can be implemented. For example, in a constant current mode shown in FIG. 6A, electronic control system 200 can be operated to actively adjust the applied potential between cathode elements 110 and extraction gate 120 over the length of each pulse in order to maintain a constant output current at a desired amplitude. In one aspect, the output current can be maintained at an output current that deviates not more than about 1 to 5 percent of a desired output current.

Such adjustments can be required to maintain a constant current output since CNT field emission cathodes are known to degrade over time. This means that over the lifetime of cathode elements 110, an increasingly higher potential difference between cathode elements 110 and extraction gate 120 can be required in order to achieve the same output current. To account for this degradation, electronic control system 200 can update the initial potential difference defined by the stored I-V data based on the information on the applied potential difference and the measured current during the pulse, and it can adjust the pulse from each of cathode elements 110 to enable consistent performance over the life of the cathode elements 110. More specifically, for example, electronic control system 200 can measure emission characteristics (e.g., output current) of cathode elements 110 (step 502). These measurements can be made at one of more of cathode elements 110 individually, or a total measurement for all of cathode elements 110 can be obtained. If the emission characteristics of all cathode elements are measured together, adjustable series resistors can be provided to compensate for performance differences in the individual cathode elements.

Regardless of how the emission characteristics are measured, the potential difference between extraction gate 120 and at least one of cathode elements 110 can be adjusted from the initial set point based on this information (step 503). In this mode of operation, it can be preferable that electronic control system 200 can regulate the emission characteristics of cathode elements 110 to within about 1 to 5 percent of the desired values.

Alternatively, in a dose control mode shown in FIG. 6B, the initial potential difference established by electronic control system 200 can define a pulse having a pre-determined current amplitude. During the pulse, the integral of the emission current over time (e.g., the product of the current multiplied by time for simple pulses) can be continuously measured (step 504 in FIG. 6B), and as soon as the integral equals a desired value (i.e., a dose amount is reached), the pulse can be terminated (step 505). In this mode, the preset pulse length can determine the maximum pulse length allowed. Based on the given values, electronic control system 200 can select the current amplitude in order to achieve the desired integral within the given pulse length window. In this way, no active regulation of the applied potential is required.

For many applications, especially in medical imaging x-ray, accurate dose information is important. A large capacitive spike in the beginning of the pulse can often be observed when measuring the output current of cathode elements 110 as a function of time along the pulse. This capacitive spike is not equal to the current that passes to anode 140, however, so an adjustment can be made to the dose calculation to account for this spike. For example, when measuring the output current at cathode elements 110, the initial current spike can be ignored for the purpose of determining the dose. This adjustment method can work particularly well for long pulses, but the transmission rate through the gate has to be known. For example, for short pulses the initial current spike can be subtracted from measured signal if the shape of the spike is known.

In addition to dealing with degradation of cathode elements 110, it can be further desirable to guard against other factors that can detrimentally affect the operation of cathode elements 110. For example, when high energy electrons transmitted from cathode elements 110 hit anode 140, ions and secondary electrons can be released. From this release, positively charged ions can travel back to cathode elements 110 and can damage field emission film 114. Such ion release can also trigger more severe arcing events that result in a large ion current towards cathode elements 110 and/or a subsequent change in potential between cathode elements 110 and extraction gate 120. For instance, when the applied potential to extraction gate 120 is raised, a high current can be extracted from cathode elements 110 for a short time, which can lead to cathode damage.

Figure 7A:
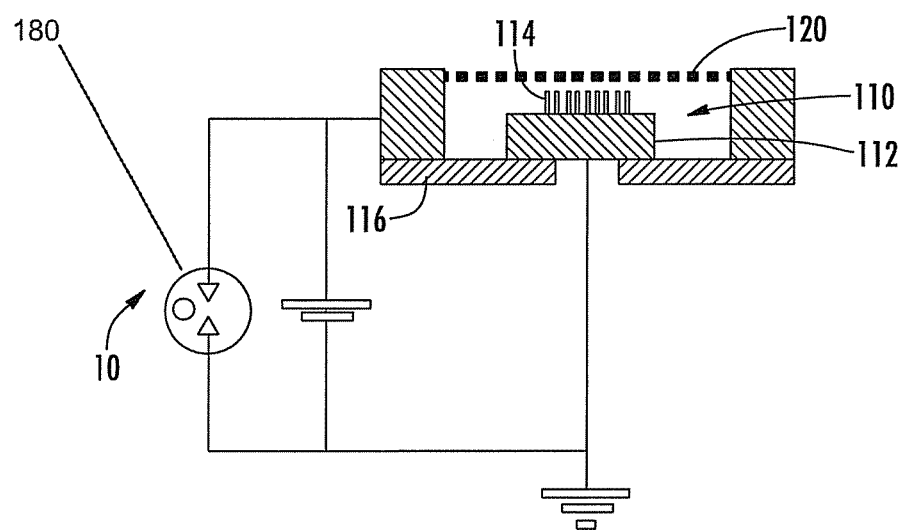
FIGS. 7A through 7C are side views of field emission cathodes in a variety of configurations according to embodiments of the presently disclosed subject matter.
Figure 7B:
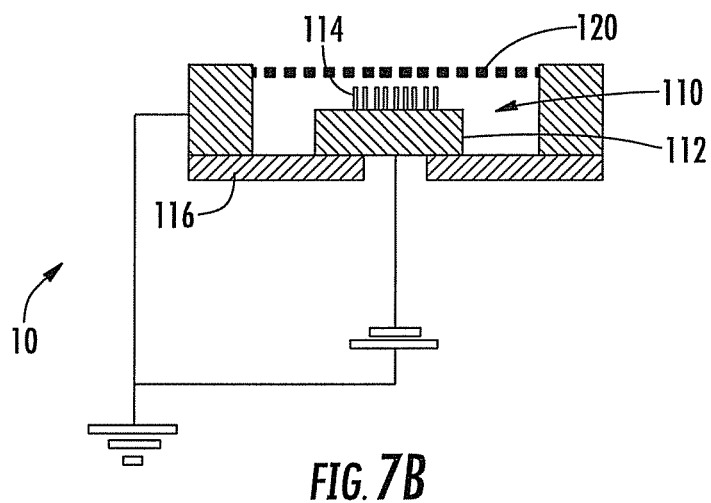
Figure 7C:
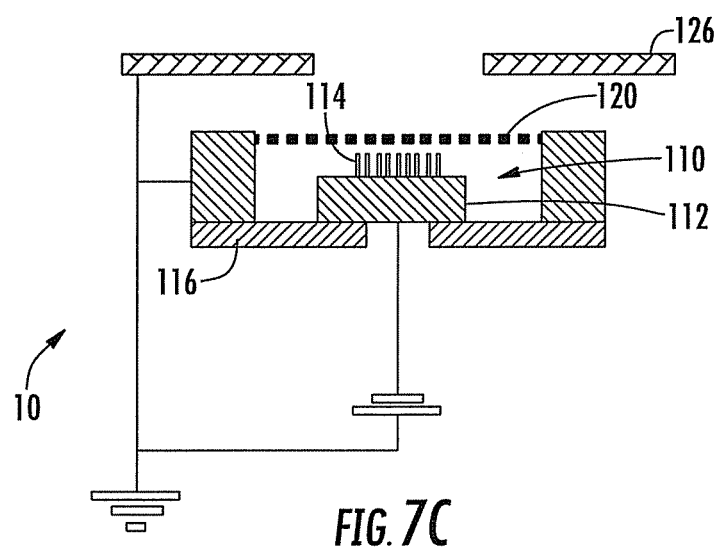

To help protect cathode elements 110 from these and other potential modes of damage, any of a variety of protection mechanisms can be implemented. First, for example, FIG. 7A illustrates a configuration in which a gas discharge tube 180 can be positioned between extraction gate 120 and cathode elements 110 to limit the maximum potential difference between the elements. Alternatively, as illustrated in FIG. 7B, extraction gate 120 can be grounded well with vacuum housing, and cathode elements 110 can be put on negative potential relative to extraction gate 120. In yet another alternative shown in FIG. 7C, a second electrode 126 can be placed between extraction gate 120 and anode 140. In still another example, extraction gate 120 can be supplied with a negative voltage. These exemplary protection mechanisms can be applied individually or in combination.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method for performing an x-ray scan comprising:
   providing a multibeam field emission x-ray system comprising a plurality of cathode elements, an anode assembly spaced from the plurality of cathode elements, and an extraction gate positioned between the plurality of cathode elements and the anode assembly;
   applying a potential difference between the extraction gate and at least one of the plurality of cathode elements to cause an emission of electrons from the respective cathode elements;
   measuring emission characteristics of the plurality of cathode elements; and
   adjusting the potential difference between the extraction gate and at least one of the plurality of cathode elements based on the emission characteristics measured.

2. The method of claim 1, wherein applying a potential difference between the extraction gate and at least one of the plurality of cathode elements comprises connecting the extraction gate to a ground potential and applying a negative potential to the at least one of the plurality of cathode elements.

3. The method of claim 1, wherein measuring emission characteristics comprises measuring an output current of the plurality of cathode elements.

4. The method of claim 3, wherein adjusting the potential difference based on the emission characteristics measured comprises adjusting the potential difference to maintain a substantially constant output current.

5. The method of claim 4, wherein the output current is maintained at an output current that deviates not more than about 1 to 5 percent of a desired output current.

6. The method of claim 3, wherein measuring emission characteristics of the plurality of cathode elements comprises measuring integral of the emission current over time supplied by the multibeam field emission X-ray system; and
   wherein adjusting the potential difference based on the emission characteristics measured comprises stopping the emission of electrons when the integral equals a desired value.

7. The method of claim 6, wherein the emission of electrons is stopped when the integral of the emission current over time is within about 1 to 5 percent of a desired value.

8. The method of claim 1, comprising focusing electrons emitted from the plurality of cathode elements towards the anode assembly.

9. The method of claim 1, comprising synchronizing application of a potential difference between the extraction gate and at least one of the plurality of cathode elements with a system master that controls an imaging or treatment device.

10. The method of claim 1, wherein:
    the extraction gate comprises a plurality of gate segments, each gate segment corresponding to a subset of the plurality of cathode elements; and
    applying a potential difference between the extraction gate and at least one of the plurality of cathode elements comprises applying a potential difference between at least one of the plurality of cathode elements and a corresponding gate segment.

11. The method of claim 1, wherein applying a potential difference between the extraction gate and at least one of the plurality of cathode elements comprises independently regulating the potential difference between the extraction gate and each of the plurality of cathode elements.

12. A multibeam field emission x-ray system comprising:
    a plurality of cathode elements;
    an anode assembly spaced from the plurality of cathode elements;
    an extraction gate positioned between the plurality of cathode elements and the anode assembly; and
    an electronic control system configured to control an application of a potential difference between the extraction gate and at least one of the plurality of cathode elements to cause an emission of electrons from the respective cathode elements, to measure emission characteristics of the plurality of cathode elements, and to adjust the potential difference between the extraction gate and at least one of the plurality of cathode elements based on the emission characteristics measured.

13. The multibeam field emission x-ray system of claim 12, wherein each of the cathode elements comprising an electrically conductive substrate with a nanostructure film deposited onto the substrate, the substrate being attached to an electrically insulating material.

14. The multibeam field emission x-ray system of claim 13, wherein the nanostructure film comprises a carbon nanotube based film.

15. The multibeam field emission x-ray system of claim 12, wherein the extraction gate is connected to a ground potential; and
    wherein the electronic control system configured to apply a negative potential to the at least one of the plurality of cathode elements.

16. The multibeam field emission x-ray system of claim 12, wherein the anode assembly comprises an anode-side collimator.

17. The multibeam field emission x-ray system of claim 12, wherein:
    the extraction gate comprises a plurality of gate segments, each gate segment corresponding to a subset of the plurality of cathode elements; and
    the electronic control system is separately connected to each of the gate segments for independent control of the potential difference between each of the gate segments and the corresponding subset of the plurality of cathode elements.

18. The multibeam field emission x-ray system of claim 17, wherein a separate electronic control system is connected to each of the gate segments.

19. The multibeam field emission x-ray system of claim 12, wherein the plurality of cathode elements, the extraction gate, and the anode assembly are contained in a vacuum housing, the vacuum housing comprising electrical feedthroughs for making electrical connections to one or more of the cathode elements, the extraction gate, and the anode assembly.

20. The multibeam field emission x-ray system of claim 12, wherein the electronic control system is separately connected to each of the plurality of cathode elements for independent control of each of the plurality of cathode elements.

21. The multibeam field emission x-ray system of claim 12, comprising a focusing structure associated with each of the plurality of cathode elements and positioned between the plurality of cathode elements and the anode assembly.

22. The multibeam field emission x-ray system of claim 12, comprising a system master that controls an imaging or treatment device, the system master being in communication with the electronic control system via an electrical interface.

23. The multibeam field emission x-ray system of claim 22, wherein the electrical interface comprises real-time signals for synchronizing operation of the electronic control system with the system master.

24. The multibeam field emission x-ray system of claim 22, wherein the electrical interface comprises a data channel for transferring information between the electronic control system and the system master.

* * * * *